United States Patent
Peschel et al.

(10) Patent No.: US 6,570,026 B1
(45) Date of Patent: May 27, 2003

(54) METHOD FOR PRODUCING PHTHALIC ANHYLIC ANHYDRIDE ACCORDING TO SPECIFICATIONS

(75) Inventors: Werner Peschel, Freinsheim (DE); Bernd Bessling, Grünstadt (DE); Peter Reuter, Mannheim (DE); Peter Michael Lorz, Wachenheim (DE); Bernhard Ulrich, Bockenheim (DE); Jean Werner Knab, Limburgerhof (DE); Matthias Kummer, Weisenheim (DE); Thomas Rühl, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/049,858

(22) PCT Filed: Aug. 10, 2000

(86) PCT No.: PCT/EP00/07759

§ 371 (c)(1),
(2), (4) Date: Feb. 19, 2002

(87) PCT Pub. No.: WO01/14308

PCT Pub. Date: Mar. 1, 2001

(30) Foreign Application Priority Data

Aug. 20, 1999 (DE) ......................................... 199 39 629

(51) Int. Cl.⁷ ............................................. C07D 307/89
(52) U.S. Cl. ........................... 549/307; 203/41; 203/86
(58) Field of Search ............................ 549/307; 203/41, 203/86

(56) References Cited

U.S. PATENT DOCUMENTS

| | | | |
|---|---|---|---|
| 3,420,750 A | 1/1969 | Schaefer et al. | 203/72 |
| 4,008,255 A | 2/1977 | Wirth et al. | 260/346 |
| 4,165,324 A | 8/1979 | Schroeder et al. | 260/346 |
| 4,547,578 A | 10/1985 | Gude et al. | 549/250 |

FOREIGN PATENT DOCUMENTS

| | | |
|---|---|---|
| DE | 198 24 532 | 12/1999 |
| WO | WO 00/53561 | 9/2000 |

OTHER PUBLICATIONS

Ruhroel "Phtalsäureanhydrid" Europa–Chemie (1965) pp. 7.
Suter "Phtalsäureanhudrid Und Siene Verwengung" (1972) pp. 38–45.
Encyclopedia of Chemical Technology Fourth Edition vol. 18 (1996) pp. 997–1006.
Ullmann's Encyclopedia of Industrial Chemistry Fifth Edition vol. A20 (1992) pp. 181–189.

*Primary Examiner*—Taofiq Solola
(74) *Attorney, Agent, or Firm*—Keil & Weinkauf

(57) ABSTRACT

On-spec phthalic anhydride is prepared by distillative purification of crude phthalic anhydride by a process in which crude phthalic anhydride is fed to a distillation column which is operated at reduced pressure, the low boilers are removed at the top or in the vicinity of the top of the distillation column and the on-spec phthalic anhydride is removed from the column via a side take-off.

14 Claims, 1 Drawing Sheet

METHOD FOR PRODUCING PHTHALIC ANHYLIC ANHYDRIDE ACCORDING TO SPECIFICATIONS

Figure 1:
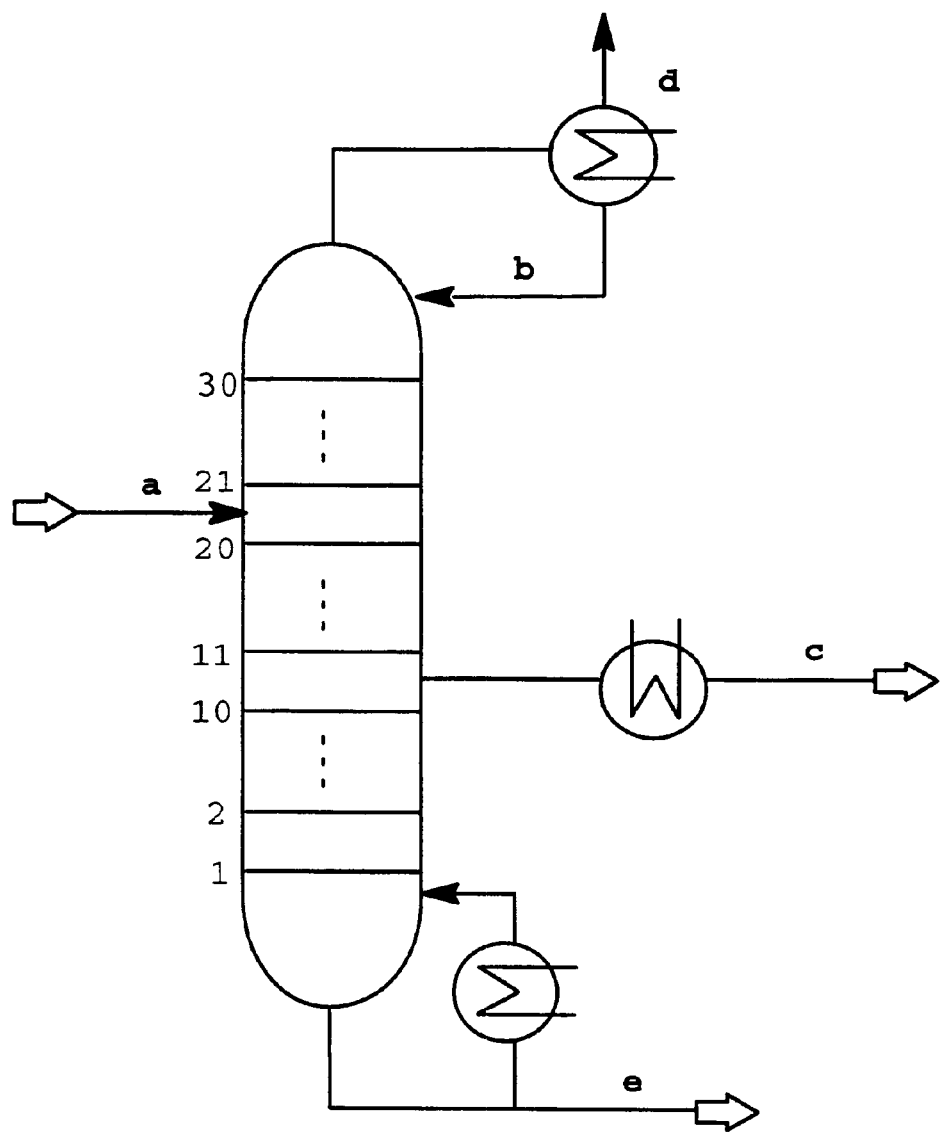

This application is a 371 of PCT/EP00/07759 filed Aug. 10, 2000.

The present invention relates to a process for the preparation of on-spec phthalic anhydride by distillative purification of crude phthalic anhydride.

Phthalic anhydride is a key chemical of the chemical industry. It is used in considerable quantities as a starting material for dialkyl phthalates, which are employed in large amounts as a plasticizer for plastics such as PVC. Crude phthalic anhydride is produced industrially from naphthalene and/or o-xylene by catalytic oxidation in the gas phase. Preferably a crude phthalic anhydride prepared in this manner from o-xylene is used. The discharges of these processes usually contain more than 99.5% by weight, based on their total weight, of phthalic anhydride. The phthalic anhydride is generally isolated in liquid form or as a solid on separators and then usually purified by distillation. For this purpose, it is fed to the distillation column in liquid form or after vaporization.

Depending on the chosen preparation process and in particular on the starting materials and the catalysts, the product in each case contains a specific range of impurities and byproducts (cf. for example H. Suter: "Wissenschaftliche Forschungsberichte: II. Anwendungstechnik und angewandte Wissenschaft", Dr. Dietrich Steinkopff Verlag, Darmstadt, 1972, page 39 etc.; abbreviated below to "Suter").

On the market, a phthalic anhydride quality having the following specification limits is expected:

Solidification point (° C.) min. 130.8
Mass fractions (% by weight):
    phthalic anhydride min. 99.8
    maleic anhydride max. 0.05
    benzoic acid max. 0.10 or max. 0.01 in the case of food quality
    phthalic acid max. 0.1
Melt color number (Hazen) max. 20
Heat color number (Hazen) max. 40

Because a phthalic anhydride without discoloring impurities is required for most intended uses, characterization by the color numbers—primarily the melt color number and the heat color number—is particularly important. Color changes of the phthalic anhydride under thermal load are of practical importance because phthalic anhydride is usually stored and transported in the molten state—at about 160° C.

In industry, over the long period in which phthalic anhydride has been produced on an industrial scale, the removal of these byproducts by means of distillation has become established (cf. for example: "Ullmann's Encyclopedia of Industrial Chemistry", 5th. Edition, Vol. A20, VCH Verlagsgesellschaft mbH, Weinheim, 1992, pages 181 to 189; abbreviated below to "Ullmann"; Kirk-Othmer "Encyclopedia of Chemical Technology", 4th. Edition, Vol. 18, John Wiley & Sons, New York, 1996, pages 997 to 1006, abbreviated below to "Kirk-Othmer"). Low-boiling and/or azeotropic impurities, some having an intense natural color, present a person skilled in the art with considerable problems, in spite of comparatively small amounts. In practice, the procedure therefore adopted in industry is to subject the crude phthalic anhydride to combined purification comprising thermal pretreatment and distillation.

The thermal pretreatment is carried out at 220–280° C. and with a residence time in the reactor of from several hours to a day. The other boundary conditions of the thermal pretreatment depend in general on the origin and hence composition of the crude phthalic anhydride. It serves various purposes familiar to a person skilled in the art; for example, the byproduct phthalic acid is evidently dehydrated to give the desired product phthalic anhydride, which, even at low contents of phthalic acid, is of considerable economic importance in view of the large industrially produced amounts of phthalic anhydride. The water formed or other water is removed in the thermal pretreatment because it may interfere with the subsequent distillation. Furthermore, certain byproducts of the synthesis reaction are converted into resins by the thermal pretreatment, which facilitates the subsequent distillative purification of the phthalic anhydride (cf. for example "Suter", pages 41–45). In the thermal pretreatment, it is also possible to add certain chemical substances in order to change the range of byproducts selectively before the distillation step.

The distillation—especially when it is effected by continuous method frequently of particular interest from economic points of view—is usually carried out by means of two columns in order to obtain a sufficiently pure phthalic anhydride. In the first step, as a rule the low boilers (for example benzoic acid, maleic anhydride and citraconic anhydride) i.e. substances having a boiling point below the boiling point of the phthalic anhydride, are separated off; in a second step, phthalic anhydride is then distilled off from the high boilers (for example, phthalic acid, certain color-imparting components, condensates of ingredients of the crude phthalic anhydride), i.e. substances having higher boiling points than the boiling point of phthalic anhydride or of undistillable components.

In "Suter" (loc. cit., page 45) reference is already made to a one-stage continuous distillation of phthalic anhydride (Ruhröl, Europa-Chemie 21, 7 (1965)), no further details being mentioned.

In summary, it may be said that the purification of crude phthalic anhydride is a very expensive process with respect to the plant and operating costs, especially if it is a question of obtaining the product quality required for many practical applications. The thermal pretreatment step has nevertheless been retained to date in industry in spite of the associated higher costs.

It is an object of the present invention to provide a technically simple and hence economical process by means of which crude phthalic anhydride can be purified so that the specifications demanded on the market are achieved.

We have found that this object is achieved by a process for the preparation of on-spec phthalic anhydride by distillative purification of crude phthalic anhydride, in which crude phthalic anhydride is fed to a distillation column which is operated at reduced pressure, the low boilers are removed at the top or in the vicinity of the top of the distillation column and the on-spec phthalic anhydride is removed from the column via a side take-off.

By means of the novel process it is possible, without the thermal pretreatment which has become usual in industry, to obtain a phthalic anhydride of high purity which fulfils the generally known specifications of pure phthalic anhydride or even surpasses them in particular in the color numbers: as a rule, a phthalic anhydride having a melt color number of less than 10 APHA and a heat color number of less than 20 APHA is obtained.

Suitable distillation columns (also abbreviated below to "columns") in the context of the present invention are tray columns, columns containing dumped packings and columns containing stacked packings as well as columns in which the technical features of these column types have been combined. Tray columns are preferably used. Conventional internals, such as commercial trays, packings, for example bubble trays, tunnel trays, valve trays, sieve trays, dual-flow trays and lattice trays, Pall-Ringe®, Berl® saddles, wire mesh rings, Raschig-Ringe®, Intalox® saddles Interpak® packings and Intos®, as well as stacked packings, for example Sulzer-Mellapak®, Sulzer-Optiflow®, Kühni-Rombopak® and Montz-Pak®,and fabric packings, can be used in said column types. In the region below the column feed, internals which are also suitable for solids are preferably chosen, particularly dual-flow trays. Trays and packings of the abovementioned designs are generally suitable for this purpose.

The column is generally equipped with a bottom evaporator and also with a condenser at the top of the column.

The diameter of the column depends on the throughputs strived for in each case and can be readily determined by a person skilled in the art according to the conventional rules of industry.

The height of the column and the positions of feed and side take-off can be determined using the concept of the number of theoretical plates in conjunction with the internals chosen.

A theoretical plate is defined as that column unit which concentrates the readily volatile component according to the thermodynamic equilibrium, assuming that ideal mixing is present, both phases are in equilibrium and there is no entrainment of liquid drops (cf. Vauck, Müller: Grundoperationen chemischer Verfahrenstechnik, VCH Verlagsgesellschaft mbH, Weinheim, 1988).

In general, the novel column is divided into three sections which are determined by the positions of feed, side take-off, top and bottom. The number of theoretical plates for the upper two sections and the reflux of the column are determined according to the usual process and engineering considerations, depending on the low-boiler fraction in the crude phthalic anhydride and the desired residual content of low boilers in the purified phthalic anhydride. The number of theoretical plates for the lower section of the novel column is in general from 1 to 10, preferably from 2 to 8, especially from 3 to 7.

The novel process is particularly suitable for crude phthalic anhydride as obtained by catalytic gas-phase oxidation of o-xylene and preferably containing more than 95, particularly more than 98% by weight of phthalic anhydride.

The column is generally operated at an absolute pressure at the top of the column of from 0.05 to 0.5, preferably from 0.1 to 0.3, particularly preferably from 0.15 to 0.25, very particularly preferably about 0.2, bar. The temperatures in the column are in general from about 160 to 230° C. at the top of the column and from 180 to 270° C. at the bottom of the column. The temperature at the side take-off is in general from 170 to 260° C., preferably from 200 to 240° C.

The distillation can be carried out batchwise or, preferably, continuously. The crude phthalic anhydride is fed to the column preferably in liquid or gaseous form or in particular in liquid form. Removal in liquid form is usually effected above the column feed, and removal in gaseous form, which is preferred, is usually effected below the feed.

In a preferred embodiment of the novel process with the use of tray columns, technical means such as drop separators can be mounted at the side take-off either inside or outside the column.

It is found particularly advantageous to use a tray column in which the tray below and the tray above the point at which the side take-off is located are a distance apart which is greater than the usual distance between the trays in the column, preferably by from one to five times, in particular from two to three times, the side take-off preferably being located closer to the upper of the two trays.

In a preferred process variant, the column trays are arranged in such a way that the lowermost tray is arranged higher by an amount of from 1 to 6, preferably from 2 to 4, particularly preferably 3, times the distance between the trays in the column, compared with the usual position in the column. In this process variant, the plant availability and the reliability of the quality are further improved.

Usually, the lowermost tray of a column is arranged a certain distance away from the vapor pipe of the bottom evaporator. It has been found that, in the case of column trays installed in the usual position, considerable encrustations occurred on the lowermost 6, in particular on the lowermost 3, trays during operation to carry out the novel process and could be mechanically removed only with difficulty. Considerable encrustations also occurred in the downpipes of said lowermost trays, as well as considerable deposits and loose coke-like fragments of different sizes in the vapor pipe of the bottom evaporator. A considerable pressure drop of up to 130 mbar was found over the lowermost highly soiled trays, which pressure drop increased with increasing duration of operation. Surprisingly, it has been found that the considerable soiling described above and the resulting problems associated therewith during operation of the column could furthermore be avoided by arranging the lowermost tray appropriately high, as described above.

A further improvement of the novel process, in particular with regard to the soiling problem, can be achieved if, in a preferred embodiment, at least the lowermost 1 to 6, preferably 2 to 4, particularly preferably 3, trays are in the form of dual-flow trays. It is furthermore preferable if at least the trays below the side take-off are in the form of dual-flow trays. However, it is also possible for all trays below the feed of the crude phthalic anhydride to be in the form of dual-flow trays.

A further improvement of the novel process envisages that the bottom evaporator of the column is designed as a falling-film evaporator. As a rule, forced-circulation flash evaporators are used as bottom evaporators for columns for the distillation of phthalic anhydride. On the other hand, falling-film evaporators are not used by those skilled in the art if the liquid to be treated contains solids (as in the present case), owing to the danger of the possible blockage of the pipes. Surprisingly, it has been found that this known problem did not occur and that the apparatus had no deposits. In the cold pipes, only gray acicular crystals were found, essentially of condensed phthalic anhydride, which could readily be knocked off the pipe walls. Falling-film evaporators are generally known in process engineering. They have the advantages of a short average residence time of the liquid in the evaporation region, resulting in gentle evaporation compared with forced-circulation flash evaporators. Owing to the gentler treatment, it was possible to reduce the tendency to solids formation, and the short residence times led to a reduction in undesired secondary reactions and hence to an improved yield in the bottom, and the operating costs could be reduced.

The on-spec phthalic anhydride is usually cooled directly after removal from the column and is obtained as liquid or, after solidification, as a solid. A higher purity can, if desired, be achieved by subjecting the phthalic anhydride to precision distillation, for example via a side column, or by mounting a dividing wall axially above a certain region in the column (i.e. Petlyuk arrangement). Recrystallization is also suitable here.

Via the side take-off, the on-spec phthalic anhydride is usually removed in an amount of at least 97% by weight, based on the weight of the feed. In continuous operation of the column, the amount removed is preferably at least 90, particularly preferably at least 95% by weight, based on the weight of the feed.

The recovery of phthalic anhydride is as a rule 98% or higher, based on the content in the feed stream to the column.

The low boilers obtained under distillation, and high boilers, are usually incinerated.

If desired, one or more chemical substances which according to general technical knowledge are capable of reducing the proportion of undesired impurities, in particular those which complicate the separation of substances in the distillation, may also be added to the crude phthalic anhydride before or during the distillation. Examples are alkali metal hydroxide, for example for reducing the phthalide content (cf. U.S. Pat. No. 4,165,324), sodium bicarbonate, sulfuric acid, boric acid or mixtures of sulfuric acid and boric acid. The use of such additives is not part of the invention.

Of course, the novel process can also be optimally adapted for individual separation problems. This adaptation can be carried out routinely by a person skilled in the art if he follows the disclosed teachings.

The purity of the phthalic anhydride thus obtained can be determined by generally known analytical methods, such as gas chromatography, UV spectroscopy and acid-based titration. In particular, the melt color number (APHA/Hazen color scale, cf. W. Liekmeier, D. Thybusch: Charakterisierung der Farbe von klaren Flüssigkeiten, Editor: Bodenseewerk Perkin-Elmer GmbH, Überlingen, 1991) is generally determined by determining the color number of phthalic anhydride immediately after sampling at 160° C. Furthermore, the heat color number is generally determined by keeping the phthalic anhydride at 250° C. for 90 minutes and then measuring the color number.

EXAMPLE 1

A tray column according to the schematic FIG. 1 was used. The column had 30 bubble trays (roughly 18 theoretical plates) and had a diameter of 50 mm. The side take-off was located between the 10th and the 11th tray above the bottom (roughly in the region between the fifth and the sixth theoretical plate), and the feed was located between the 20th and the 21st tray above the bottom (roughly in the region of the eleventh theoretical plate). In FIG. 1, the 1st and the 2nd tray are also shown, and the other trays are indicated by perpendicular broken lines.

The crude phthalic anhydride distilled was one which had been prepared by gas-phase oxidation of o-xylene over a fixed bed in the presence of a catalyst consisting of a support coated with the catalytically active metal oxides cesium oxide (calculated as 0.4% by weight of cesium), vanadium oxide (4% by weight) and titanium dioxide (95.6% by weight) (cf. the prior German patent application with file reference 198 24 532). The loading in the reactor was 86 g of o-xylene per $m^3$ (S.T.P.) of air. The reactor temperature was from 350 to 450° C.

The crude phthalic anhydride thus obtained had the following composition:

99.24% by weight of phthalic anhydride 0.2% by weight of benzoic acid 200 ppm by weight of maleic anhydride 20 ppm by weight of citraconic anhydride 0.5% by weight of phthalic acid and the remainder to 100% by weight comprising other substances.

1000 g/h of this crude phthalic anhydride were fed continuously (a) to the column. With a reflux of 600 g (b), an absolute pressure of 0.2 bar at the top of the column, a temperature of 200° C. at the top of the column and 228° C. at the bottom of the column, 980 g of purified phthalic anhydride were removed in the same time via the side take-off at 224° C., condensed and isolated (c). The top take-off via (d) was condensed in a cold trap and amounted to about 5 g; the bottom take-off via (e) amounted to about 15 g and contained the high boilers and undistillable matter. The analysis of the phthalic anhydride isolated via the side take-off at (c) gave the following composition:

99.97% by weight of phthalic anhydride 30 ppm by weight of benzoic acid

<10 ppm by weight of maleic anhydride

<10 ppm by weight of citraconic anhydride 0.025% by weight of phthalic acid and the remainder to 100% by weight comprising other substances.

The melt color number was determined immediately after removal and was 5–10 APHA. The heat color number was determined as follows: a sample of phthalic anhydride was heated in an oven for 1.5 hours at 250° C. The color number was then measured as 10–20 APHA.

EXAMPLE 2

Starting from the following specifications with respect to crude product and pure product:

0.3% by weight of benzoic acid in phthalic anhydride to be purified by the novel distillation process and 10 ppm of benzoic acid in the pure product having an otherwise unchanged composition of the crude phthalic anhydride compared with Example 1, the configuration of the tray column to be used was modified in the following manner:

Number of trays between gaseous side take-off (stream c) and top of column: equivalent to 19 theoretical plates, Number of trays between feed (stream c) and top of column: equivalent to 8 theoretical plates, Number of trays between bottom of column and gaseous side take-off (stream c): 10 dual-flow trays, Absolute pressure at top of column about 70 mbar, Temperature in bottom of column: from 230 to 240° C., Design of the bottom evaporator: falling-film evaporator, Distance between side take-off (stream c) and the tray underneath and closest to said side take-off: 3 times the usual tray spacing in the column and Distance from vapor pipe of the bottom evaporator to the first tray arranged above it: 3 times the usual tray spacing in the column in addition to the usual distance between the lowermost tray and the vapor pipe of the bottom evaporator.

What is claimed is:

1. A process for the preparation of on-spec phthalic anhydride by distillative purification of crude phthalic anhydride, wherein crude phthalic anhydride is fed to a distillation column which is operated at reduced pressure, the low boilers are removed at the top or in the vicinity of the top of the distillation column and the on-spec phthalic anhydride is removed from the column via a side take-off.

2. A process as claimed in claim 1, wherein the distillation is carried out at a pressure at the top of the column of from 0.05 to 0.5 bar.

3. A process as claimed in claim 1, wherein the distillation is carried out in a tray column.

4. A process as claimed in claim 3, wherein the tray below and the tray above the point at which the side take-off is located are a distance apart which is up to 5 times greater than the usual distance between the trays in the column.

5. A process as claimed in claim 4, wherein the side take-off is preferably located closer to the upper of the two trays.

6. A process as claimed in claim 1, wherein the on-spec phthalic anhydride is removed from the column in gaseous form via a side take-off.

7. A process as claimed in claim 1, wherein the lowermost tray is arranged higher by an amount of up to 6 times the distance between the trays in the column, compared with the usual position in the column.

8. A process as claimed in claim 3, wherein at least the lowermost 1 to 6 trays are in the form of dual-flow trays.

9. A process as claimed in claim 8, wherein at least the trays below the side take-off are in the form of dual-flow trays.

10. A process as claimed in claim 1, wherein a falling-film evaporator is used as the bottom evaporator for the distillation column.

11. A process as claimed in claim 8, wherein the lowermost tray is arranged higher by an amount of from 2 to 4 times the distance between the trays in the column, compared with the usual position in the column.

12. A process as claimed in claim 8, wherein the lowermost tray is arranged higher by an amount of 3 times the distance between the trays in the column, compared with the usual position in the column.

13. A process as claimed in claim 8, wherein at least the lowermost 2 to 4 trays are in the form of dual-flow trays.

14. A process as claimed in claim 8, wherein at least the lowermost 3 trays are in the form of dual-flow trays.

* * * * *